United States Patent
Chen et al.

(10) Patent No.: US 10,266,523 B2
(45) Date of Patent: Apr. 23, 2019

(54) CRYSTALINE FORMS OF N-[6-(CIS-2,6-DIMETHYLMORPHOLINE-4-YL)PYRIDINE-3-YL]-2-METHYL-4'-(TRIFLUOROMETHOXY) [1,1'-BIPHENYL]-3-METHANAMIDE MONOPHOSPHATE, AND PROCESS OF PREPARATION THEREOF

(71) Applicant: CRYSTAL PHARMATECH CO., LTD., Suzhou, Jiangsu (CN)

(72) Inventors: Minhua Chen, Jiangsu (CN); Yanfeng Zhang, Suzhou (CN); Fei Lu, Suzhou (CN); Xiaoyu Zhang, Suzhou (CN)

(73) Assignee: CRYSTAL PHARMATECH CO., LTD., Suzhou (CN)

( * ) Notice: Subject to any disclaimer, the term of this patent is extended or adjusted under 35 U.S.C. 154(b) by 0 days.

(21) Appl. No.: 15/579,881

(22) PCT Filed: Mar. 30, 2016

(86) PCT No.: PCT/CN2016/077886
§ 371 (c)(1),
(2) Date: Dec. 5, 2017

(87) PCT Pub. No.: WO2016/155630
PCT Pub. Date: Oct. 6, 2016

(65) Prior Publication Data
US 2018/0170919 A1 Jun. 21, 2018

(30) Foreign Application Priority Data
Mar. 30, 2015 (CN) .......................... 2015 1 0144499

(51) Int. Cl.
A61K 31/5377 (2006.01)
C07D 413/04 (2006.01)
A61P 35/00 (2006.01)

(52) U.S. Cl.
CPC ........ C07D 413/04 (2013.01); A61K 31/5377 (2013.01); A61P 35/00 (2018.01); C07B 2200/13 (2013.01)

(58) Field of Classification Search
CPC .......................... A61K 31/5377; C07D 413/04
USPC ....................................... 514/235.5; 544/124
See application file for complete search history.

(56) References Cited

U.S. PATENT DOCUMENTS 8,178,563 B2 * 5/2012 Gao .................. C07C 235/56
514/352
2012/0122866 A1 5/2012 Fritze et al.

FOREIGN PATENT DOCUMENTS

| WO | 2010033481 A1 | 3/2010 |
| WO | 2014128661 A1 | 8/2014 |
| WO | 2017163258 A1 | 9/2017 |

OTHER PUBLICATIONS

Shifeng Pan, et al., Discovery of NVP-LDE225, a Potent and Selective Smoothened Antagonist, ACS Medicinal Chemistry Letters, 2010. I, pp. 130-134.

* cited by examiner

*Primary Examiner* — Brenda L Coleman
(74) *Attorney, Agent, or Firm* — VLP Law Group LLP; Kent H. Cheng

(57) ABSTRACT

The present disclosure relates to novel crystalline forms of N-[6-(cis-2,6-dimethylmorpholine-4-yl)pyridine-3-yl]-2-methyl-4'-(trifluoromethoxy)[1,1'-biphenyl]-3-carboxamide monophosphate, and process of preparation thereof. The crystalline form of the monophosphate of a compound of formula (I) has low hygroscopicity, is convenient to store, has better stability than that of diphosphonate in prior art, can avoid the risk of crystal transformation in the development and production of the drug. The preparation method is simple, has low cost, and has important value for further optimization and development of the drug.

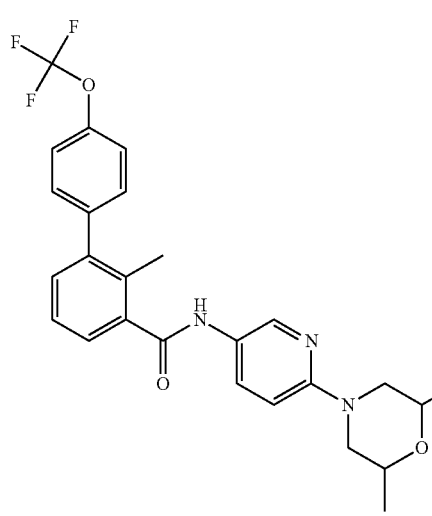

(I)

22 Claims, 5 Drawing Sheets

CRYSTALINE FORMS OF N-[6-(CIS-2,6-DIMETHYLMORPHOLINE-4-YL)PYRIDINE-3-YL]-2-METHYL-4'-(TRIFLUOROMETHOXY)[1,1'-BIPHENYL]-3-METHANAMIDE MONOPHOSPHATE, AND PROCESS OF PREPARATION THEREOF

TECHNICAL FIELD

The present disclosure relates to the field of pharmaceutical chemistry, particularly relates to crystalline forms of N-[6-(cis-2,6-dimethylmorpholine-4-yl)pyridine-3-yl]-2-methyl-4'-(trifluoromethoxy)[1,1'-biphenyl]-3-carboxamide monophosphate, crystalline forms and process of preparation thereof.

BACKGROUND

LDE225 (Sonidegib, Erismodegib) is a Smoothenced (SMO) target inhibitor developed by Novartis, and the drug is in multiple clinical trials for various diseases, including myelofibrosis, leukemia and solid tumors, such as basal cell carcinoma, angiocarcinoma, pancreatic cancer, breast cancer and non-small cell lung cancer. The chemical name of LDE225 is N-[6-(cis-2,6-dimethylmorpholine-4-yl)pyridine-3-yl]-2-methyl-4'-(trifluoromethoxy)[1,1'-biphenyl]-3-carboxamide, and the structure is shown as formula (I).

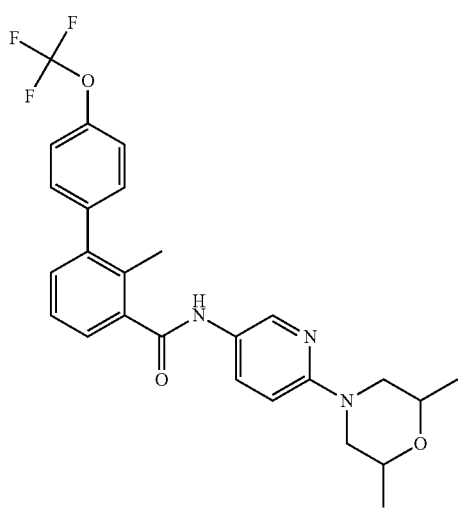

(I)

Different crystalline forms of the same compound are significantly different in appearance, solubility, melting point, dissolution rate, bioavailability and so on, thus affect stability, bioavailability and efficiency of drugs. Therefore, it is of great significance to develop new crystalline forms that are more suitable for drug development.

As is known to the skilled in the art, the presence of new solid polymorphic forms of a known chemical substance is unpredictable. The existence of the polymorphic compound or the number of the polymorphic forms is also unpredictable. In addition, it is also unpredictable under what conditions to obtain a specific form, and how are the characteristics of the polymorphic form. Since the properties of each polymorph of the compound (e.g., solubility, stability) cause the difference of use and storage, it is necessary to study all solid forms, including all polymorphic forms to provide drugs with improved storage stability or predictable solubility.

At present, CN10241249A disclosed crystalline Form A and Form B of free base of compound of formula (I), and CN102159570B disclosed crystalline forms of diphosphonate, monohydrochloride and monosulfate of compound of formula (I). Diphosphonate can increase the dissolution rate of free base and has relatively high in-vivo exposure, thus it is a preferred choice for drug development. However, CN102159570B disclosed that the XRPD of the crystalline form of diphosphonate is slightly changed, after it has been placed at 50° C./75% RH (relative humidity) for 2 weeks. The XRPD of the crystalline form of diphosphonate is changed after it has been placed at 80° C./75% RH for two weeks. Therefore, there is risk that the more preferred diphosphonate in prior art will have crystal transformation in transportation and storage.

The inventors of the present disclosure have surprisingly found two crystalline forms of compound of formula (I) monophosphate, and the diphosphonate disclosed in CN102159570B is not stable in solvents containing water or a biological medium, the diphosphonate would disproportionate and generate phosphoric acid in solvents containing water, which has a certain effect on the pH of in-vivo environment. Therefore, there is a need to find new crystalline forms which are stable in solvents containing water or biological media. The present disclosure shows that the stability of the monophosphate is better than that of diphosphonate, and the crystalline form A and crystalline form B of the monophosphate have homogeneous particle size and the dispersion is good. The monophosphate provided by the present disclosure has smaller molecular weight than that of the diphosphonate, and thus has higher content of active ingredients, so it can reduce dose and save cost, and is more suitable for drug development.

The crystalline forms of monophosphate in present disclosure have good stability and low hygroscopicity, good for storing, can avoid crystal transformation in the development and production of the drug. In addition, the monophosphate has similar solubility with that of diphosphonate, and has strong developing and economic value.

SUMMARY

The present disclosure provides compound of formula (I) monophosphate, two crystalline forms of the monophosphate and the process of preparation thereof. The novel crystalline forms provided by the present disclosure are suitable for drug research and industrial production.

One objective of the disclosure is to provide a monophosphate crystalline form of compound of formula (I), and the process of preparation thereof.

In particular, the solid form in the present disclosure is designated as crystalline Form A.

In particular, the crystalline Form A of the present disclosure, wherein the X-ray powder diffraction pattern shows characteristic peaks at 2theta values of 17.5°±0.2°, 5.1°±0.2° and 13.0°±0.2°.

Furthermore, the crystalline Form A of the present disclosure, wherein the X-ray powder diffraction pattern shows one or two or three characteristic peaks at 2theta values of 18.0°±0.2°, 16.3°±0.2° and 24.4°±0.2°. Preferably, the crystalline Form A of the present disclosure, wherein the X-ray powder diffraction pattern further shows characteristic peaks at 2theta values of 18.0°±0.2°, 16.3°±0.2° and 24.4°±0.2°.

Furthermore, the crystalline Form A of the present disclosure, wherein the X-ray powder diffraction pattern of shows one or two or three characteristic peaks at 2theta values of 20.5°±0.2°, 9.8°±0.2° and 13.9°±0.2°. Preferably, the crystalline Form A of the present disclosure, wherein the X-ray powder diffraction pattern further shows characteristic peaks at 2theta values of 20.5°±0.2°, 9.8°±0.2° and 13.9°±0.2°.

Preferably, the crystalline Form A of the present disclosure, wherein the X-ray powder diffraction pattern of shows characteristic peaks at 2theta values of 17.5°±0.2°, 5.1°±0.2°, 13.0°±0.2°, 18.0°±0.2°, 16.3°±0.2°, 24.4°±0.2°, 20.5°±0.2°, 9.8°±0.2° and 13.9°±0.2°.

Furthermore, the crystalline Form A of the present disclosure, wherein the X-ray powder diffraction pattern is substantially as depicted in FIG. 1.

The crystalline Form A of the present disclosure, wherein the differential scanning calorimetry (DSC) thermogram shows an endothermic peak when heated to around 215° C. (onset temperature), and the DSC thermogram is substantially as depicted in FIG. 2.

The crystalline Form A of the present disclosure, wherein the thermal gravimetric analysis (TGA) thermogram of crystalline Form A shows about 0.7% weight loss when heated to 150° C., and the TGA thermogram is substantially as depicted in FIG. 3.

Another objective of the present disclosure is to provide a process of preparing crystalline Form A of monophosphate of formula (I), wherein the process comprises reacting the compound of formula (I) with concentrated phosphoric acid in water or solvents containing water, and drying the obtained solid at 100° C.-200° C.

Furthermore, said solvents containing water comprise, but are not limited to solvents of alcohols, ketones, esters, aromatic hydrocarbons, halogenated hydrocarbons, nitriles, cyclic ethers, aliphatic hydrocarbons mixed with water.

The present disclosure further provides another process of preparing crystalline Form A of monophosphate of formula (I), wherein the process comprises adding the hydrochloride of compound of formula (I) into one or more solvent selected from the group of water, alcohols, ketones, acids, esters or nitriles, and then adding sodium hydroxide solution, stirring to obtain a solid, reacting the obtained solid with concentrated phosphoric acid in water or solvents containing water, then drying the obtained solid at the temperature of 100-200° C. Preferably, said alcohol is preferably methanol, said solvents containing water comprise, but are not limited to solvents of alcohols, ketones, esters, aromatic hydrocarbons, halogenated hydrocarbons, nitriles, cyclic ethers, aliphatic hydrocarbons mixed with water.

Another objective of the disclosure is to provide a crystalline form of a monophosphate of formula (I), designated as Form B.

The crystalline Form B of the present disclosure, wherein the X-ray powder diffraction pattern shows characteristic peaks at 2theta values of 19.2°±0.2°, 9.7°±0.2° and 16.5°±0.2°.

Furthermore, the crystalline Form B of the present disclosure, wherein the X-ray powder diffraction pattern shows one or two or three characteristic peaks at 2theta values of 19.6°±0.2°, 29.6°±0.2° and 12.6°±0.2°. Preferably, the crystalline Form B of the present disclosure, wherein the X-ray powder diffraction pattern further shows characteristic peaks at 2theta values of 19.6°±0.2°, 29.6°±0.2° and 12.6°±0.2°.

Furthermore, the crystalline Form B of the present disclosure, wherein the X-ray powder diffraction pattern shows one or two or three characteristic peaks at 2theta values of 17.2°±0.2°, 15.4°±0.2° and 25.0°±0.2°. Preferably, the crystalline Form B of the present disclosure, wherein the X-ray powder diffraction pattern further shows characteristic peaks at 2theta values of 17.2°±0.2°, 15.4°±0.2° and 25.0°±0.2°.

Preferably, the X-ray powder diffraction pattern of crystalline Form B shows characteristic peaks at 2theta values of 19.2°±0.2°, 9.7°±0.2°, 16.5°±0.2°, 19.6°±0.2°, 29.6°±0.2°, 12.6°±0.2°, 17.2°±0.2°, 15.4°±0.2° and 25.0°±0.2°.

Furthermore, the crystalline Form B of the present disclosure, wherein the X-ray powder diffraction pattern is substantially as depicted in FIG. 4.

The crystalline Form B of the present disclosure, wherein the differential scanning calorimetry (DSC) thermogram shows endothermic peaks when heated to around 120° C., 200° C. and 212° C. (onset temperature), and the DSC thermogram is substantially as depicted in FIG. 5.

The crystalline Form B of the present disclosure, wherein the thermal gravimetric analysis (TGA) thermogram of crystalline Form B shows about 8.6% weight loss when heated to 100° C., and the TGA thermogram is substantially as depicted in FIG. 6.

Another objective of the present disclosure is to provide a process of preparing crystalline Form B of monophosphate of formula (I), wherein the process comprises reacting the compound of formula (I) with concentrated phosphoric acid in water or solvents containing water, and drying the obtained solid at 50° C.-80° C.

Furthermore, solvents containing water comprise, but are not limited to solvents of alcohols, ketones, esters, aromatic hydrocarbons, halogenated hydrocarbons, nitriles, cyclic ethers, aliphatic hydrocarbons mixed with water.

The present disclosure provides another process of preparing crystalline Form B of monophosphate of formula (I), wherein the process comprises adding the hydrochloride of compound of formula (I) into one or more solvent selected from the group of alcohols, ketones, acids, esters or nitriles, then stirring and crystallizing at the temperature of 50-80° C.

Furthermore, said acid is acetic acid, said nitrile is acetonitrile, said ketone is acetone.

Another objective of the present disclosure is to provide a process of preparing crystalline Form B of monophosphate of formula (I), wherein the process comprises adding the hydrochloride of compound of formula (I) into one or more solvent selected from the group of water, alcohols, ketones, acids, esters or nitriles, then adding sodium hydroxide solution, stirring to obtain a solid, reacting the obtained solid with concentrated phosphoric acid in water or solvents containing water, then drying the obtained solid at the temperature of 50-80° C.

Furthermore, said alcohol is methanol, said solvents containing water comprise, but are not limited to solvents of alcohols, ketones, esters, aromatic hydrocarbons, halogenated hydrocarbons, nitriles, cyclic ethers, aliphatic hydrocarbons mixed with water.

Another object of the disclosure is to provide a pharmaceutical composition comprising an effective amount of the monophosphate of formula (I), crystalline Form A of monophosphate, crystalline Form B of monophosphate, or a combination thereof and pharmaceutically acceptable carrier, diluent or excipient. Generally, mix or contact therapeutically an effective amount of monophosphate of formula (I), crystalline Form A, crystalline Form B or a combination thereof with one or more pharmaceutical adjuvants to make pharmaceutical composition or formulation, and the pharmaceutical composition or formulation are prepared by well-known method in the pharmaceutical field.

Furthermore, monophosphate of formula (I), crystalline Form A, crystalline Form B, or a combination thereof of the present disclosure can be used for preparing drugs for treating cancer, especially for preparing drugs for treating basal cell carcinoma and solid tumor.

The pharmaceutical composition can be developed into a certain dosage form, and is administrated by a suitable route, such as oral administration and parenteral administration (including subcutaneous, muscle, vein or skin), rectal, transdermal, nasal and vagina, and so on. The dosage form suitable for oral administration comprises tablets, capsules, granules, powder and pills, a powder, an ingot, a solution, a syrup or a suspension according to needs, and can be used for rapid release, delayed release or regulation release of active pharmaceutical ingredients. The dosage form suitable for parenteral administration comprises an aqueous or non-aqueous sterile injection solution, an emulsion or a suspension. The dosage form suitable for rectal administration comprises a suppository or an enema. The dosage form suitable for transdermal administration comprises an ointment, a cream and a patch. The dosage form suitable for nasal administration comprises an aerosol, a spray and a nose drop. The dosage form suitable for vaginal administration comprises a suppository, a plugging agent and a gel, a paste or a spray. Preferably, the crystalline forms of the present disclosure is especially suitable for preparing a tablet, a suspension, a capsule, a disintegrating tablet, an immediate release and controlled release tablet, and further preferably is a tablet, a suspension and a capsule.

The pharmaceutically acceptable excipient in the pharmaceutical composition is in the condition of a solid oral dosage form, including but not limited to: a diluent, such as starch, pregelatinized starch, lactose, powdery cellulose, microcrystalline cellulose, calcium hydrophosphate, tricalcium phosphate, mannitol, sorbitol, sugar and so on; an adhesive, such as arabic gum, guar gum, gelatin, polyvinylpyrrolidone, hydroxypropyl cellulose, hydroxypropyl methyl cellulose, polyethylene glycol and so on; a disintegrating agent, such as starch, sodium hydroxyacetate, pregelatinized starch, cross-linked povidone, cross-linked sodium carboxymethyl cellulose and colloidal silica; a lubricant, such as stearic acid, magnesium stearate, zinc stearate, sodium benzoate, sodium acetate and the so on; a glidants, such as colloidal silica and so on; a compound forming agent, such as various levels of cyclodextrin and resin; a release rate control agent, such as hydroxypropyl cellulose, hydroxymethyl cellulose, hydroxypropyl methyl cellulose, ethyl cellulose, methyl cellulose, methyl methacrylate, wax and so on. Other pharmaceutically acceptable excipients include but are not limited to: a film-forming agent, a plasticizer, a coloring agent, a flavoring agent, a viscosity regulator, a preservative, an antioxidant and the so on. Preferably, the tablet is coated with a coating layer, for example, providing shellac isolation coating, sugar coating or polymer coating, wherein the coating layer comprises a polymer such as hydroxypropyl methyl cellulose, polyvinyl alcohol, ethyl cellulose, methacrylic acid polymer, hydroxypropyl cellulose or starch, and can also comprise an anti-sticking agent such as silicon dioxide, talcum powder, an emulsion agent such as titanium dioxide, a colorant such as an iron oxide colorant. In the case of a liquid oral dosage form, the appropriate excipient comprises water, oils, alcohols and glycols, a preservative, a stabilizer, a coloring agent and so on. The water or the non-water sterile suspension can contain a suspending agent and a thickening agent. The excipient that is suitable for the water-based suspension comprises synthetic rubber or natural rubber such as arabic gum, xanthium gum, alginate, glucan, sodium carboxymethyl cellulose, methylcellulose, polyvinylpyrrolidone or gelatin. In the case of parenteral administration, the excipient of the water or non-aqueous sterile injectable solution is generally sterile water, normal saline or a glucose aqueous solution, which can contain a buffering agent, an antioxidant, a bacteriostatic agent and a solute capable of enabling the pharmaceutical composition to be combined with blood. Each excipient must be acceptable, and can be compatible with other ingredients in the formula and is harmless to a patient.

The pharmaceutical composition can be prepared by methods known to those skilled in the art in prior art. When the pharmaceutical composition is prepared, the crystalline forms of the disclosure are combined with one or more pharmaceutically acceptable carriers, diluent or excipient, and are optionally mixed with one or more other pharmaceutical active ingredients. For example, tablets, capsules and granules can be prepared by mixing, granulating, tableting, filling capsules and so on, the powder is prepared by mixing the medicinal active ingredients and the excipient which are finely ground into a proper size, the solution and the syrup can be prepared by dissolving the active ingredients of the medicines in a properly flavored water or solvents containing water, and the suspension can be prepared by dispersing the active ingredients of the drugs in pharmaceutically acceptable carriers.

The crystalline form A and the crystalline form B of the monophosphate of compound of formula (I) provided by the disclosure can be used for treating cancers of bladder, breast, colon, kidney, liver, lung (including small cells and non-small cell lung cancer, and lung adenocarcinoma), ovary, prostate, testis, urinary genital tract, lymph system, rectum, throat, pancreas, esophagus, stomach, gall bladder, cervix uteri, thyroid and skin. The central nervous system and peripheral nervous system tumors comprise astrocytoma, neuroblastoma, glioma, medulloblastoma and schwannoma. The tumors of the interstitial source comprise fibrosarcoma, rhabdomyosarcoma and osteosarcoma. Other tumors comprise melanoma, mekel cell carcinoma, coloring dry skin disease, keratoacanthoma, seminoma, thyroid follicular carcinoma and teratoma. The present disclosure can also be used for the treatment of mastocytosis, germ cells tumors, pediatric sarcomas and other cancers The present disclosure can also be used for inhibiting the growth and proliferation of lymphoid hematopoietic tumors, such as leukemia, including acute lymphocytic leukemia (ALL), acute lymphoblastic leukemia, B-cell lymphoma, T-cell lymphoma, Hodgkin's lymphoma, non-Hodgkin's lymphoma, hairy cell lymphoma, tissue cell lymphoma and Burkitt's lymphoma, and ematopoietic tumors of myeloid lineage, including acute and chronic myelogenous leukemias, myelodysplastic syndrome and promyelocytic leukemia.

The disclosure relates to a method of treatment of a dermatological disease, disorder or condition mediated by the hedgehog signaling pathway (particularly selected from the group consisting of a hyperproliferative skin condition, or Gorlin's syndrome, basal cell carcinoma, sebaceous hyperplasia and psoriasis), which treatment comprises administering to a subject in need of such treatment, particularly a human, an effective amount of crystalline Form A of monophosphate and form B of the as described herein.

The term "effective amount" or "therapeutically effective amount" as used herein means that amount of an active compound that elicits the biological or medicinal response in a tissue, system, animal or human that is being sought by a researcher, veterinarian, medical doctor, or other clinician.

As used herein, the term "treatment" refers to one or more of the following: (1) Preventing disease, for example, preventing the disease, illness or disorder in an individual who may be suffering from a disease, illness or disorder but not suffering from or displaying a lesion or symptom of the disease, (2) Inhibiting the disease, for example, inhibiting the disease, illness or disorder in an individual who is suffering from or displaying a lesion or symptom of the disease, illness or disorder, and (3) Improving the disease, for example, improving the disease, illness or disorder in an individual who is suffering from or displaying a lesion or symptom of the disease, illness or disorder (that is to reverse the lesion and/or symptoms), for example, reducing the severity of the disease.

As used herein, the term "polymorphic form" refers to different crystalline forms of the same compound and includes, but is not limited to other solid forms including hydrates and solvates of the same compound. The phenomenon that the same drug molecule forms a variety of crystalline forms is called drug polymorphism, drug polymorphism is a phenomenon commonly found in solid drugs. It is known that pharmaceutical compounds having such polymorphs have an influence on pharmacological activity, solubility, bioavailability and stability due to their different physical and chemical properties. Therefore, in the case where a compound useful as a drug has polymorphic forms, it is desirable to produce a crystalline compound that is more useful from these polymorphs.

The term "X-ray powder diffraction pattern" as used herein refers to a diffraction pattern observed by an experiment or a parameter derived therefrom. The X-ray powder diffraction pattern is characterized by the peak position and the peak intensity.

The present disclosure has the following advantages:

The diphosphonate disclosed in CN102159570B is not stable in solvents containing water or biological medium, and the diphosphonate disproportionate and generate phosphoric acid in solvents containing water, which has a certain effect on the pH of in-vivo environment. Therefore, there is a need to find new crystalline forms which are stable in solvents containing water or biological media. The present disclosure shows that the stability of the monophosphate is better than that of diphosphonate, and the diphosphonate disproportionates and generates phosphoric acid in solvents containing water, which has a certain effect on the pH of in-vivo environment. The monophosphate provided by the present disclosure is smaller than that of the diphosphonate in molecular weight, and thus has higher content of active ingredients, so that it can reduce dose and save cost, and is more suitable for drug development.

The crystalline forms of monophosphate in present disclosure have good stability and low hygroscopicity, is convenient to store, can avoid the risk of crystal transformation in the development and production of the drug. In addition, the monophosphate has similar solubility with that of diphosphonate, and has simple and environment-friendly process, and has strong economic value.

DETAILED DESCRIPTION OF THE DISCLOSURE

The present disclosure will be further explained by the specific embodiments, but are not intended to limit the scope of the present disclosure. The skilled in the art can make improvements to the process of preparation and the used instruments within the scope of the claims, and those improvements should be considered as falling into the scope of the present disclosure. Therefore, the protective scope of the present disclosure patent should be defined by the claims.

The abbreviations used in the disclosure are explained as follows:
XRPD: X-ray Powder Diffraction
DSC: Differential Scanning Calorimetry
TGA: Thermal Gravimetric Analysis
DVS: Dynamic Vapor Sorption
$^1$H NMR: $^1$H Nuclear Magnetic Resonance X-ray powder diffraction pattern in the present disclosure is acquired by a Panalytical Empyrean X-ray powder diffractometer. The parameters of the X-ray powder diffraction method of the present disclosure are as follows:
X-ray Reflection: Cu, Kα
Kα1 (Å): 1.540598. Kα2 (Å): 1.544426
Kα2/Kα1 intensity ratio: 0.50
Voltage: 45 (kV)
5 Current: 40 (mA)
Scan range: from 3.0 degree to 40.0 degree
Sampling step: 0.013 degree Differential scanning calorimetry (DSC) data in the present disclosure are acquired by a TA Q2000. The parameters of the differential scanning calorimetry (DSC) method of the present disclosure are as follow:
Heating rate: 10° C./min
Purge gas: nitrogen Thermal gravimetric analysis (TGA) data in the present disclosure are acquired by a TA Q5000. The parameters of the thermal gravimetric analysis (TGA) method of the present disclosure are as follow:

Heating rate: 10° C./min
Purge gas: nitrogen
Dynamic Vapor Sorption (DVS) is measured via a SMS (Surface Measurement Systems) DVS Intrinsic, using 10 mg of crystalline form. Typical Parameters for DVS test are listed below:
Temperature: 25° C.
Gas and flow rate: $N_2$, 200 mL/min
dm/dt: 0.002%/min
RH range: 0% RH to 95% RH
Stable duration: 10 min
Maximum equilibrate time: 180 min
Humidity gradient: 10%(0% RH-90% RH), 5%(90% RH-95% RH), The particle size distribution test in the present disclosure is acquired by the S3500 laser particle size analyzer of Microtrac. Microtrac S3500 is equipped with the Sample Delivery Controller. The test is carried out by wet process, and the dispersion medium is Isopar G The parameters are as follow:

| | |
|---|---|
| Size distribution: Volume distribution | Acquisition time: 10 s |
| Dispersion medium: Isopar G | Particle coordinates: Standard |
| Collection frequency: 3 | Disperse medium refractive index: 1.42 |
| Transparency: Transparent | Residual: Enabled |
| Particle refractive index: 1.59 | Flow rate: 60%* |
| Particle shape: Irregularity | Filtration: Enabled |
| Ultrasonic power: 30 W | Ultrasonic time: 30 s |

*Flow rate 60% is 60% of 65 mL/s.

Example 1

Figure 1:
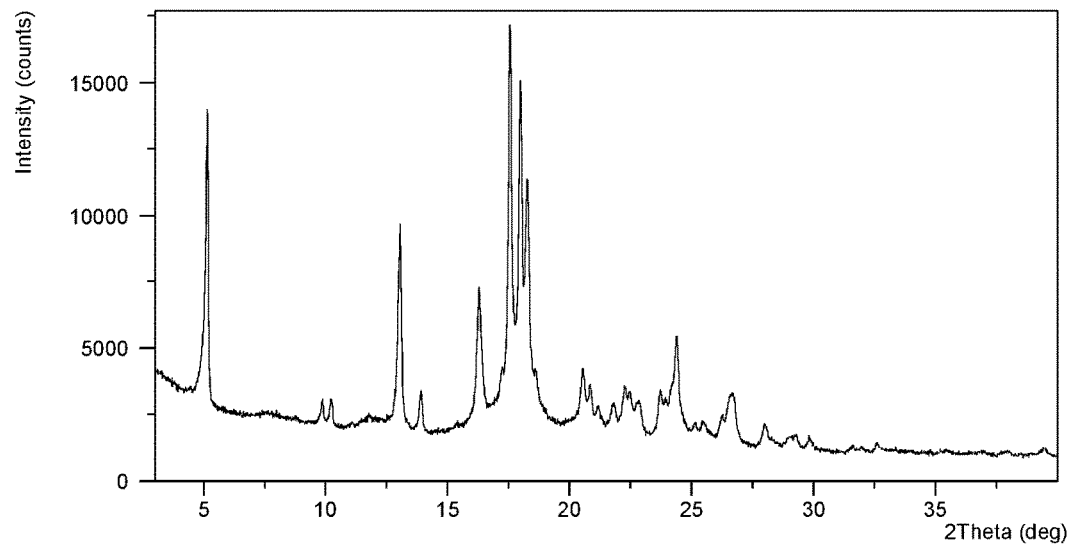
FIG. 1 shows an XRPD pattern of crystalline Form A of monophosphate.
Figure 2:
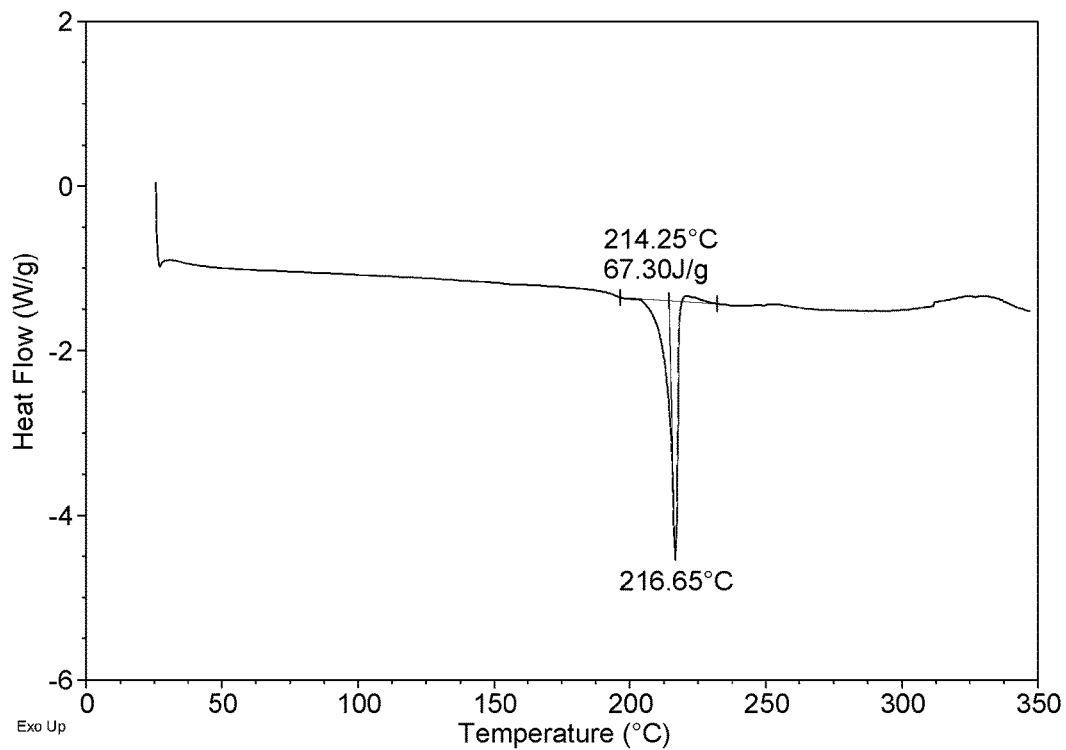
FIG. 2 shows a DSC thermogram of crystalline Form A of monophosphate.
Figure 3:
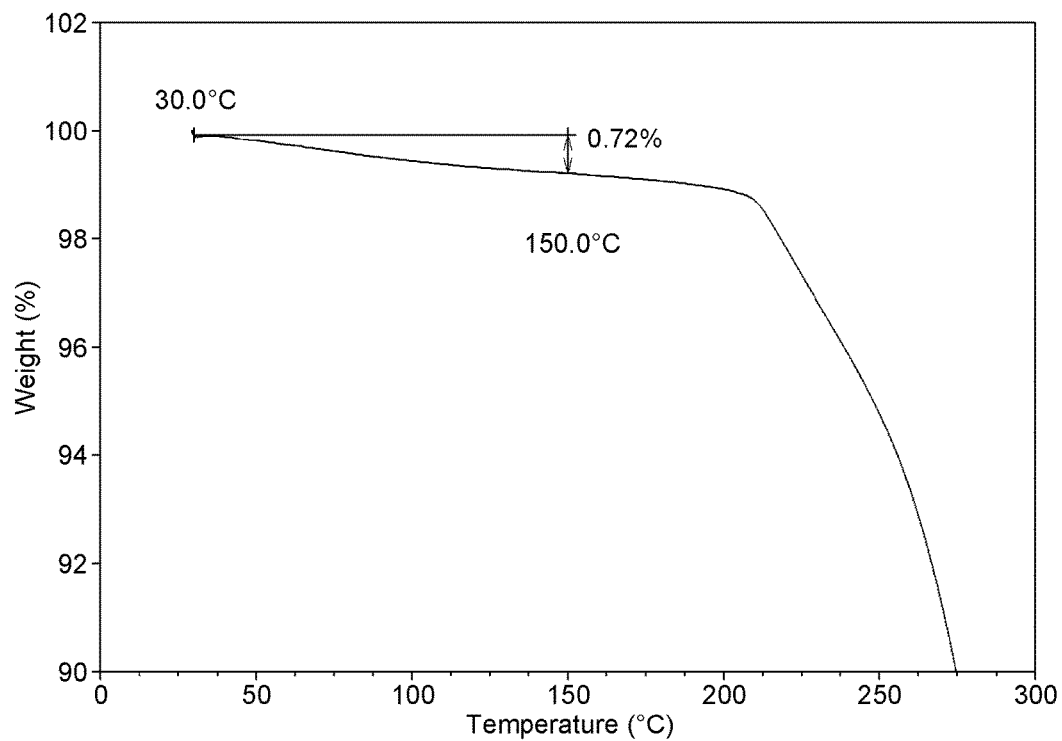
FIG. 3 shows a TGA thermogram of crystalline Form A of monophosphate.

Process of Preparing Crystalline Form A of Monophosphate of Compound of Formula (I):

221.3 mg of free base of a compound of formula (I) was dispersed in 6.0 mL of water, 0.1 mL of concentrated phosphoric acid (14.6 mol/L) was added, then it was stirred overnight and filtered. The filter cake was washed with water, and the solid was placed at a 150° C. oven for drying overnight. The obtained solid was detected as crystalline Form A of monophosphate. The XRPD data of the solid prepared in this example comprise but are not limited to Table 1. The XRPD pattern is displayed in FIG. 1. The DSC thermogram is displayed in FIG. 2, the TGA thermogram is displayed in FIG. 3.

TABLE 1

| 2theta | d spacing | Intensity % |
|---|---|---|
| 5.12 | 17.27 | 13.30 |
| 8.43 | 10.48 | 0.71 |
| 9.82 | 9.00 | 2.29 |
| 13.04 | 6.79 | 13.60 |
| 13.88 | 6.38 | 2.57 |
| 16.28 | 5.44 | 13.64 |
| 17.53 | 5.06 | 100.00 |
| 17.96 | 4.94 | 87.24 |
| 18.23 | 4.87 | 23.69 |
| 20.54 | 4.32 | 3.78 |
| 20.79 | 4.27 | 3.92 |
| 21.77 | 4.08 | 2.27 |
| 22.27 | 3.99 | 5.06 |
| 22.78 | 3.90 | 3.32 |
| 23.72 | 3.75 | 8.59 |
| 24.36 | 3.65 | 9.74 |
| 25.47 | 3.50 | 2.76 |

TABLE 1-continued

| 2theta | d spacing | Intensity % |
|---|---|---|
| 26.53 | 3.36 | 7.67 |
| 28.01 | 3.19 | 2.13 |
| 29.09 | 3.07 | 1.53 |
| 29.82 | 3.00 | 1.25 |
| 32.01 | 2.80 | 0.97 |
| 35.49 | 2.53 | 1.11 |
| 37.90 | 2.37 | 1.10 |

Example 2

Process of Preparing Crystalline Form A of Monophosphate of Compound of Formula (I):

20.4 mg of free base of compound of formula (I) was dispersed into 0.6 mL of water, two drops of 14.6 mol/L phosphoric acid was added, then it was stirred overnight and centrifuged to give a solid. The solid was placed at a 100° C. oven for drying overnight. The obtained solid was detected as crystalline Form A of monophosphate.

The XRPD data of the solid prepared in this example comprise but are not limited to Table 2.

TABLE 2

| 2theta | d spacing | Intensity % |
|---|---|---|
| 5.12 | 17.27 | 3.59 |
| 9.85 | 8.98 | 1.24 |
| 13.04 | 6.79 | 8.14 |
| 13.84 | 6.40 | 1.58 |
| 16.35 | 5.42 | 8.36 |
| 17.53 | 5.06 | 100.00 |
| 17.97 | 4.94 | 84.08 |
| 18.58 | 4.78 | 7.77 |
| 20.52 | 4.33 | 3.54 |
| 21.83 | 4.07 | 2.53 |
| 22.31 | 3.99 | 2.90 |
| 22.75 | 3.91 | 3.13 |
| 23.75 | 3.75 | 7.23 |
| 24.34 | 3.66 | 5.26 |
| 24.69 | 3.61 | 2.72 |
| 25.42 | 3.50 | 3.40 |
| 26.46 | 3.37 | 5.85 |
| 26.64 | 3.35 | 5.39 |
| 28.01 | 3.19 | 1.41 |
| 28.95 | 3.08 | 1.58 |
| 29.38 | 3.04 | 1.56 |
| 29.80 | 3.00 | 1.17 |
| 31.49 | 2.84 | 0.55 |
| 32.06 | 2.79 | 1.06 |
| 32.68 | 2.74 | 0.85 |
| 35.45 | 2.53 | 1.13 |
| 36.35 | 2.47 | 0.55 |
| 37.95 | 2.37 | 0.93 |
| 39.39 | 2.29 | 0.67 |

Example 3

Process of Preparing Crystalline Form A of Monophosphate of Compound of Formula (I):

1) 1.164 g of hydrochloride of compound of formula (I) was dissolved in 12.0 mL of methanol.
2) 0.44 g of sodium hydroxide was dissolved in 3 mL water to give a sodium hydroxide solution.
3) The sodium hydroxide solution in step 2) was added to the solution in step 1), and solid was precipitated and filtered. The filter cake was washed with water and the obtained solid was dispersed in water again.
4) 3.0 mL of 14.6 mol/L phosphoric acid was added into the solution in step 3), then it was stirred overnight and filtered. The filter cake was washed with water, and the solid was placed at a 160° C. oven for drying overnight. The obtained solid was detected as crystalline Form A of monophosphate.

The XRPD data of the solid prepared in this example comprise but are not limited to Table 3.

TABLE 3

| 2theta | d spacing | Intensity % |
|---|---|---|
| 3.11 | 28.37 | 19.54 |
| 5.12 | 17.25 | 79.83 |
| 7.54 | 11.72 | 9.99 |
| 9.85 | 8.98 | 12.38 |
| 10.22 | 8.66 | 13.01 |
| 11.83 | 7.48 | 9.01 |
| 13.03 | 6.79 | 52.67 |
| 13.89 | 6.38 | 15.03 |
| 16.27 | 5.45 | 39.14 |
| 17.18 | 5.16 | 19.79 |
| 17.53 | 5.06 | 100.00 |
| 17.96 | 4.94 | 87.18 |
| 18.24 | 4.86 | 64.34 |
| 18.59 | 4.77 | 19.65 |
| 20.54 | 4.32 | 20.47 |
| 20.82 | 4.27 | 16.39 |
| 21.16 | 4.20 | 11.47 |
| 21.80 | 4.08 | 12.22 |
| 22.26 | 3.99 | 15.88 |
| 22.45 | 3.96 | 14.95 |
| 22.82 | 3.90 | 12.24 |
| 23.72 | 3.75 | 14.73 |
| 24.37 | 3.65 | 27.74 |
| 25.13 | 3.54 | 7.51 |
| 25.46 | 3.50 | 7.87 |
| 26.24 | 3.40 | 9.24 |
| 26.52 | 3.36 | 13.30 |
| 26.68 | 3.34 | 14.36 |
| 27.98 | 3.19 | 7.50 |
| 28.95 | 3.08 | 4.35 |
| 29.24 | 3.05 | 4.74 |
| 29.81 | 3.00 | 4.02 |
| 31.56 | 2.83 | 2.11 |
| 32.60 | 2.75 | 2.88 |
| 35.39 | 2.54 | 1.12 |
| 36.89 | 2.44 | 1.06 |
| 37.92 | 2.37 | 1.08 |
| 39.44 | 2.28 | 1.57 |

Example 4

Figure 4:
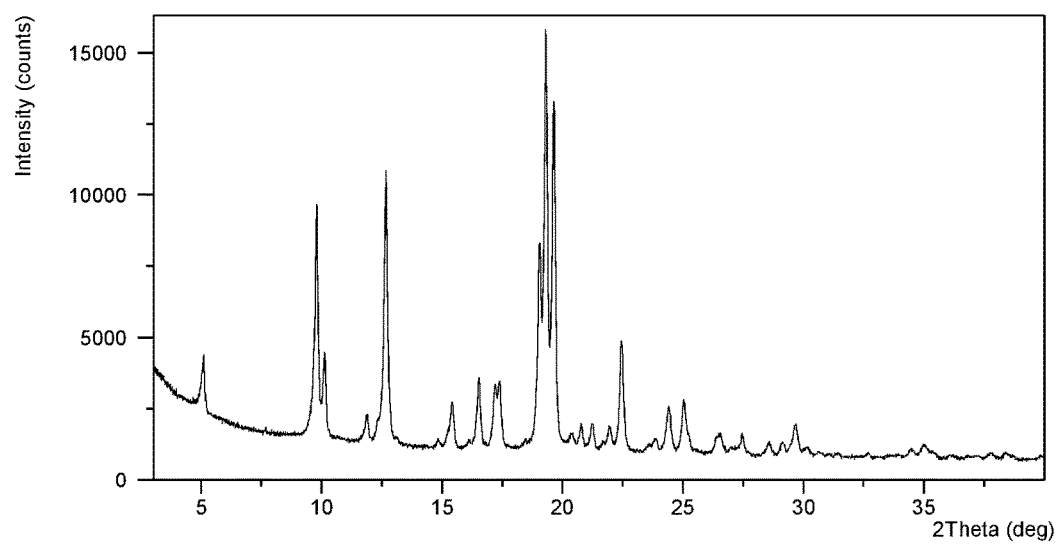
FIG. 4 shows an XRPD pattern of crystalline Form B of monophosphate.
Figure 5:
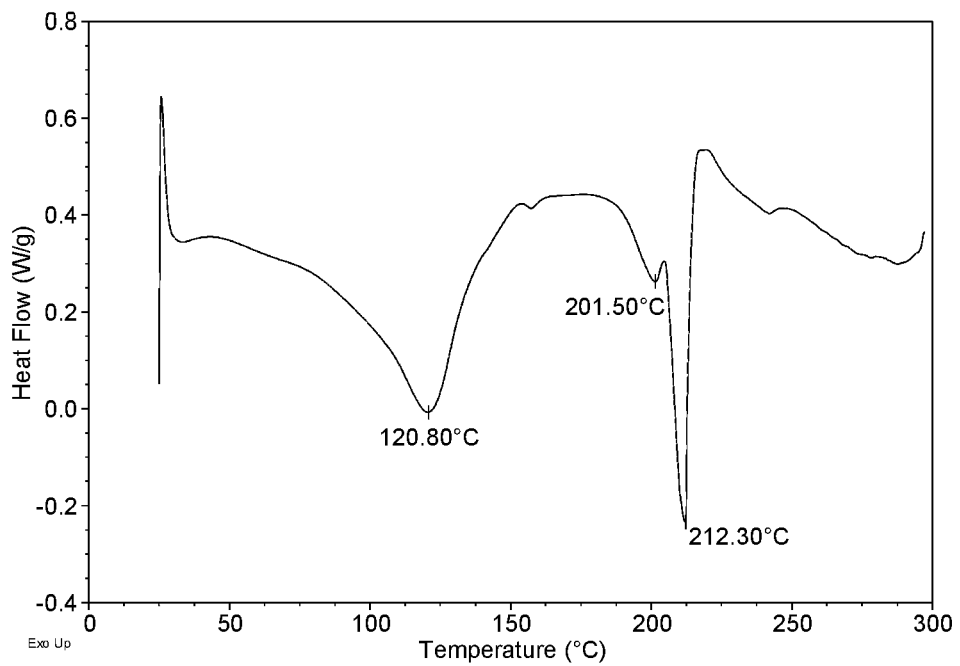
FIG. 5 shows a DSC thermogram of crystalline Form B of monophosphate.
Figure 6:
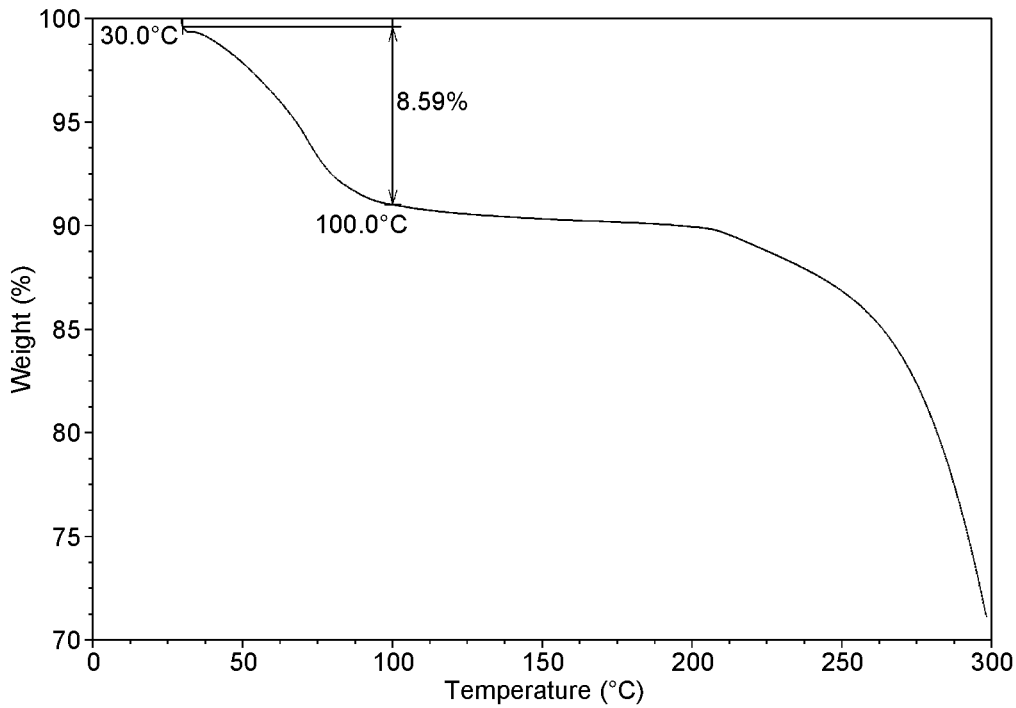
FIG. 6 shows a TGA thermogram of crystalline Form B of monophosphate.
Figure 7:
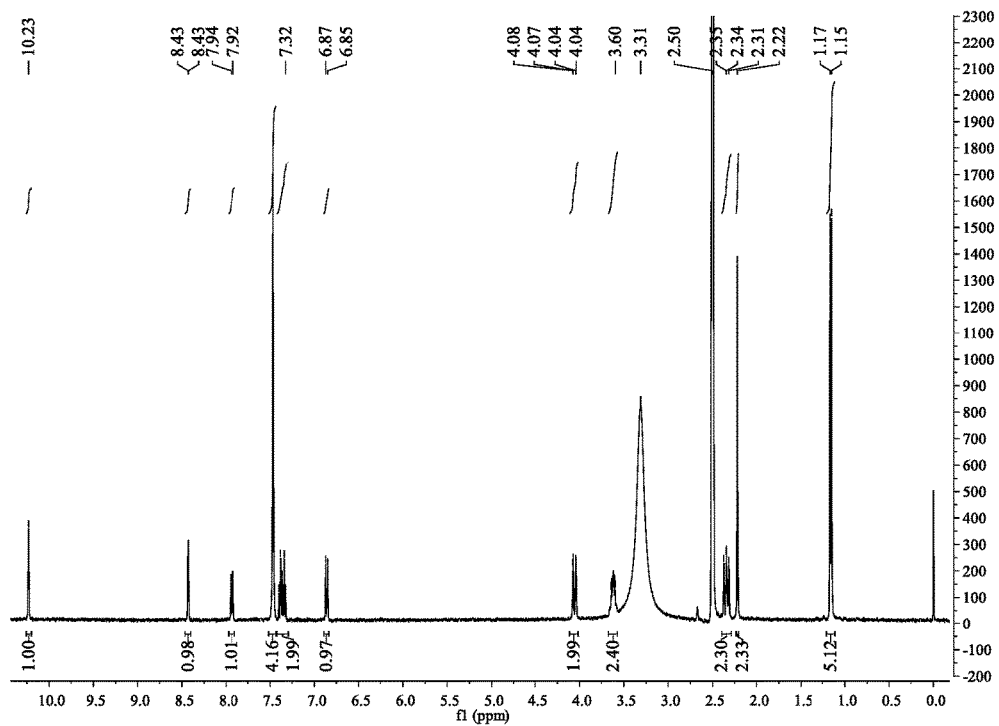
FIG. 7 shows a $^1$H NMR spectrum of crystalline Form B of monophosphate.

Process of Preparing Crystalline Form B of Monophosphate of Compound of Formula (I):

190.6 mg of free base of compound of formula (I) was added into 6.0 mL water, 0.5 mL of concentrated phosphoric acid (14.6 mol/L) was added, then it was stirred overnight and filtered. The filter cake was washed with water, and the solid was collected and placed at a 50° C. oven for drying overnight. The obtained solid was detected as crystalline Form B of monophosphate. The XRPD data of the solid prepared in this example comprise but are not limited to Table 4. The XRPD pattern is displayed in FIG. 4. The DSC thermogram is displayed in FIG. 5, the TGA thermogram is displayed in FIG. 6, the $^1$H NMR spectrum is displayed in FIG. 7.

The data of $^1$H NMR are as follows: $^1$H NMR (400 MHz, DMSO) δ 10.23 (s, 1H), 8.43 (d, J=2.6 Hz, 1H), 7.93 (dd, J=9.1, 2.7 Hz, 1H), 7.47 (s, 4H), 7.42-7.29 (m, 2H), 6.86 (d, J=9.1 Hz, 1H), 4.06 (dd, J=12.8, 1.6 Hz, 2H), 3.62 (ddd, J=10.6, 6.3, 2.5 Hz, 2H), 2.34 (dd, J=12.6, 10.6 Hz, 2H), 2.22 (s, 2H), 1.16 (d, J=6.2 Hz, 5H).

TABLE 4

| 2theta | d spacing | Intensity % |
|---|---|---|
| 4.76 | 18.58 | 1.26 |
| 9.71 | 9.11 | 27.91 |
| 11.80 | 7.50 | 2.02 |
| 12.54 | 7.06 | 13.67 |
| 15.36 | 5.77 | 2.16 |
| 16.45 | 5.39 | 4.21 |
| 17.22 | 5.15 | 5.61 |
| 18.87 | 4.70 | 18.05 |
| 19.22 | 4.62 | 100.00 |
| 19.58 | 4.53 | 78.78 |
| 21.22 | 4.19 | 4.09 |
| 22.35 | 3.98 | 15.81 |
| 23.86 | 3.73 | 1.94 |
| 25.02 | 3.56 | 8.90 |
| 27.29 | 3.27 | 4.00 |
| 28.47 | 3.13 | 1.56 |
| 29.05 | 3.07 | 3.18 |
| 29.59 | 3.02 | 8.66 |
| 30.58 | 2.92 | 1.40 |
| 34.49 | 2.60 | 2.32 |
| 34.98 | 2.57 | 3.29 |
| 38.35 | 2.35 | 0.79 |

Example 5

Process of Preparing Crystalline Form B of Monophosphate of Compound of Formula (I):

17.2 mg of solid of diphosphonate of formula (I) was dispersed into 1.4 mL acetone, and it was stirred for 2 days at 50° C. and centrifuged, the obtained solid was detected as crystalline Form B of monophosphate.

The XRPD data of the solid prepared in this example comprise but are not limited to Table 5.

TABLE 5

| 2theta | d spacing | Intensity % |
|---|---|---|
| 5.04 | 17.54 | 48.22 |
| 9.74 | 9.08 | 23.55 |
| 12.67 | 6.99 | 16.43 |
| 15.46 | 5.73 | 15.28 |
| 16.52 | 5.37 | 33.86 |
| 17.24 | 5.14 | 33.27 |
| 18.93 | 4.69 | 65.95 |
| 19.26 | 4.61 | 32.17 |
| 19.63 | 4.52 | 28.14 |
| 20.39 | 4.36 | 33.52 |
| 21.94 | 4.05 | 98.95 |
| 24.29 | 3.66 | 100.00 |
| 25.08 | 3.55 | 17.68 |
| 26.25 | 3.39 | 20.90 |
| 26.60 | 3.35 | 17.74 |
| 29.60 | 3.02 | 10.52 |
| 30.02 | 2.98 | 11.44 |
| 37.66 | 2.39 | 4.40 |

Example 6

Process of Preparing Crystalline Form B of Monophosphate of Compound of Formula (I):

1) 1.164 g of hydrochloride of compound of formula (I) was dissolved in 12.0 mL methanol.

2) 0.44 g of sodium hydroxide was dissolved in 3 mL water to give a sodium hydroxide solution.

3) The sodium hydroxide solution in step 2) was added to the solution in step 1), and solid was precipitated and filtered. The filter cake was washed with water and the obtained solid was dispersed in water again.

4) 3.0 mL of 14.6 mol/L phosphoric acid was added into the solution in step 3), then it was stirred overnight and filtered. The filter cake was washed with water, and the solid was placed at a 80° C. oven for drying overnight. The obtained solid was detected as crystalline Form B of monophosphate.

The XRPD data of the solid prepared in this example comprise but are not limited to Table 6.

TABLE 6

| 2theta | d spacing | Intensity % |
|---|---|---|
| 3.14 | 28.15 | 12.67 |
| 5.01 | 17.63 | 16.57 |
| 9.73 | 9.09 | 55.84 |
| 10.06 | 8.79 | 20.70 |
| 11.80 | 7.50 | 6.64 |
| 12.60 | 7.03 | 65.92 |
| 14.76 | 6.00 | 1.74 |
| 15.34 | 5.78 | 10.83 |
| 16.45 | 5.39 | 16.98 |
| 17.12 | 5.18 | 15.28 |
| 17.30 | 5.13 | 16.26 |
| 18.38 | 4.83 | 2.21 |
| 18.99 | 4.67 | 49.66 |
| 19.25 | 4.61 | 100.00 |
| 19.58 | 4.53 | 84.28 |
| 20.33 | 4.37 | 3.96 |
| 20.70 | 4.29 | 6.27 |
| 21.17 | 4.20 | 6.54 |
| 21.88 | 4.06 | 6.18 |
| 22.39 | 3.97 | 26.67 |
| 23.78 | 3.74 | 3.26 |
| 24.34 | 3.66 | 10.89 |
| 24.97 | 3.57 | 12.82 |
| 26.47 | 3.37 | 4.58 |
| 27.38 | 3.26 | 4.99 |
| 28.49 | 3.13 | 2.90 |
| 29.05 | 3.07 | 3.24 |
| 29.59 | 3.02 | 7.63 |
| 30.05 | 2.97 | 2.09 |
| 30.61 | 2.92 | 1.04 |
| 31.38 | 2.85 | 0.72 |
| 32.62 | 2.74 | 0.92 |
| 34.42 | 2.61 | 2.08 |
| 34.92 | 2.57 | 3.07 |
| 36.06 | 2.49 | 0.60 |
| 36.99 | 2.43 | 0.51 |
| 37.71 | 2.39 | 1.40 |
| 38.33 | 2.35 | 1.52 |

Example 7

Figure 8:
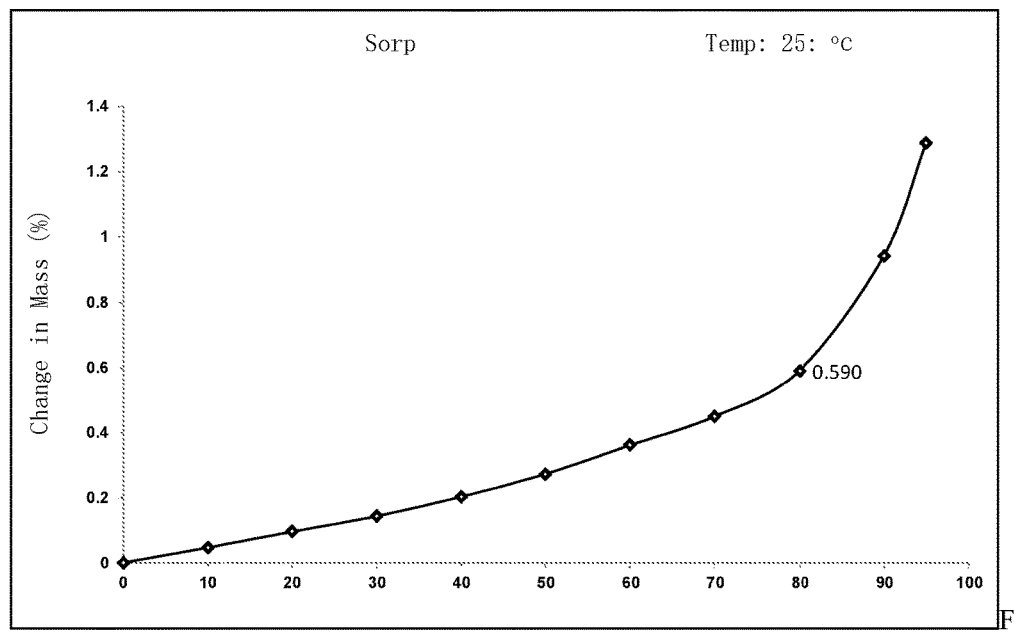
FIG. 8 shows a DVS plot of crystalline Form A of monophosphate.

Hygroscopicity Assessment of Monophosphate Form A of Compound of Formula (I):

Hygroscopicity of 10 mg of monophosphate Form A of compound of formula (I) was tested using dynamic vapor sorption (DVS). The result is listed in Table 7. The DVS isotherm plot is shown in FIG. 8.

TABLE 7

| Solid Form | Weight Gain at 80% Relative Humidity |
|---|---|
| Form A | 0.59% |

About hygroscopicity characterization description and definition of hygroscopicity (Chinese Pharmacopoeia 2010 edition appendix XIXJ Drug hygroscopic test guidelines, test at 25° C.+/−1° C., 80% Relative Humidity)

deliquescent: sufficient water is absorbed to form a liquid.
very hygroscopic: increase in mass is equal to or greater than 15%.
hygroscopic: increase in mass is less than 15% and equal to or greater than 2%.
slightly hygroscopic: increase in mass is less than 2% and equal to or greater than 0.2%.
no or almost no hygroscopic: increase in mass is less than 0.2%.

The result indicates that the weight gain of monophosphate Form A of compound of formula (I) of the present disclosure is 0.59% at 80% RH. According to the definition standard of hygroscopicity, Form A was slightly hygroscopic.

Example 8

Stability Assessment of Crystalline Form A of Monophosphate and Form B of Compound of Formula (I):

10 mg of diphosphonate in CN102159570, crystalline Form A of monophosphate and crystalline Form B of monophosphate of the present disclosure were stored under 5° C., 25° C./60% RH and 40° C./75% RH for 120 days. The samples after storage were detected by XRPD. The experiment result is shown in Table 8.

TABLE 8

| Initial Form | conditions | Storage time | Form Change |
|---|---|---|---|
| Diphosphonate in CN102159570 | 5° C. | 120 days | Diphosphonate |
| | 25° C./60% RH | 120 days | Diphosphonate |
| | 40° C./75% RH | 120 days | Diphosphonate and Form B |
| Form A | 5° C. | 120 days | Form A |
| | 25° C./60% RH | 120 days | Form A |
| | 40° C./75% RH | 120 days | Form A and Form B |
| Form B | 5° C. | 120 days | Form B |
| | 25° C./60% RH | 120 days | Form B |
| | 40° C./75% RH | 120 days | Form B |

The result indicates that diphosphonate in CN102159570 partly changed into Form B of the present disclosure, while Form B of the present disclosure remains unchanged under 40° C./75% RH for 120 days. Form B has better stability than that of diphosphonate in prior art, which will be more preferred for process development.

Example 9

Figure 9:
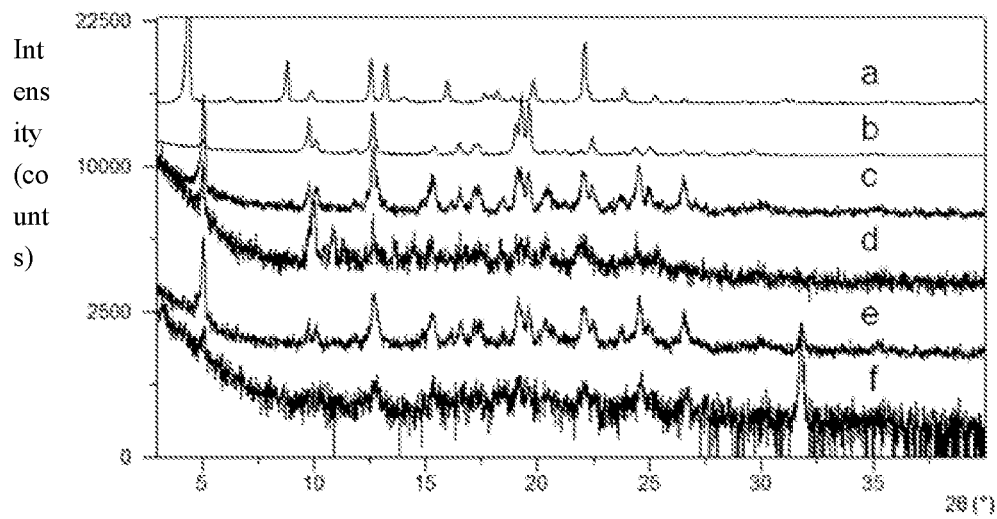
FIG. 9 shows an XRPD overlay pattern of diphosphonate of CN102159570B with crystalline Form B of monophosphate of the present disclosure in four kinds of biological media after being equilibrated for 1 hour, wherein a is starting form of diphosphonate, b is Form B of the disclosure, c is the crystalline form of the diphosphonate after 1 hour in water, d is the crystalline form of the diphosphonate after 1 hour in SGF, e is the crystalline form of the diphosphonate after 1 hour in the FaSSIF, and f is the crystalline form of the diphosphonate after 1 hour in FeSSIF.

Stability comparison of monophosphate of formula (I) and diphosphonate in CN102159570 B in the simulated biological medium:

Crystalline Form A of monophosphate and Form B of the present disclosure, and the diphosphonate of CN102159570B were prepared into saturated solution in water, SGF (Simulated gastric fluids), FaSSIF (Fasted state simulated intestinal fluids) and FeSSIF (Fed state simulated intestinal fluids). After being equilibrated for 1 hour, 4 hours and 24 hours, a small amount solid of each saturated solution was carried out for XRPD test, the testing result is shown in table 9, and the XRPD contrast diagram after 1 hour is shown in FIG. 9, wherein a is starting form of diphosphonate, b is monophosphate Form B of the present disclosure, c is the crystalline form of the diphosphonate after 1 hour in water, d is the crystalline form of the diphosphonate after 1 hour in SGF, e is the crystalline form of the diphosphonate after 1 hour in the FaSSIF, and f is the crystalline form of the diphosphonate after 1 hour in FeSSIF.

TABLE 9

Stability of three crystalline forms in the simulated biological medium

| Initial solid form | Biological medium | Equilibrium Time (h) | Final form |
|---|---|---|---|
| Diphosphonate in prior art | H$_2$O | 1 | Crystalline Form B of monophosphate |
| Diphosphonate in prior art | SGF | 1 | Crystalline Form B of monophosphate |
| Diphosphonate in prior art | FaSSIF | 1 | Crystalline Form B of monophosphate |
| Diphosphonate in prior art | FeSSIF | 1 | Crystalline Form B of monophosphate |
| Diphosphonate in prior art | H$_2$O | 4 | Crystalline Form B of monophosphate |
| Diphosphonate in prior art | SGF | 4 | Crystalline Form B of monophosphate |
| Diphosphonate in prior art | FaSSIF | 4 | Crystalline Form B of monophosphate |
| Diphosphonate in prior art | FeSSIF | 4 | Crystalline Form B of monophosphate |
| Diphosphonate in prior art | H$_2$O | 24 | Crystalline Form B of monophosphate |
| Diphosphonate in prior art | SGF | 24 | Crystalline Form B of monophosphate |
| Diphosphonate in prior art | FaSSIF | 24 | Crystalline Form B of monophosphate |
| Diphosphonate in prior art | FeSSIF | 24 | Crystalline Form B of monophosphate |
| Crystalline Form A of monophosphate | H$_2$O | 1 | Crystalline Form A of monophosphate |
| Crystalline Form A of monophosphate | SGF | 1 | Changed |
| Crystalline Form A of monophosphate | FaSSIF | 1 | Crystalline Form A of monophosphate |
| Crystalline Form A of monophosphate | FeSSIF | 1 | Crystalline Form A of monophosphate |
| Crystalline Form A of monophosphate | H$_2$O | 4 | Crystalline Form A of monophosphate |
| Crystalline Form A of monophosphate | SGF | 4 | Changed |
| Crystalline Form A of monophosphate | FaSSIF | 4 | Crystalline Form A of monophosphate |
| Crystalline Form A of monophosphate | FeSSIF | 4 | Crystalline Form A of monophosphate |
| Crystalline Form A of monophosphate | H$_2$O | 24 | Crystalline Form A of monophosphate |
| Crystalline Form A of monophosphate | SGF | 24 | Changed |
| Crystalline Form A of monophosphate | FaSSIF | 24 | Crystalline Form A of monophosphate |
| Crystalline Form A of monophosphate | FeSSIF | 24 | Crystalline Form A of monophosphate |
| Crystalline Form B of monophosphate | H$_2$O | 1 | Crystalline Form B of monophosphate |
| Crystalline Form B of monophosphate | SGF | 1 | Crystalline Form B of monophosphate |
| Crystalline Form B of monophosphate | FaSSIF | 1 | Crystalline Form B of monophosphate |
| Crystalline Form B of monophosphate | FeSSIF | 1 | Crystalline Form B of monophosphate |
| Crystalline Form B of monophosphate | H$_2$O | 4 | Crystalline Form B of monophosphate |
| Crystalline Form B of monophosphate | SGF | 4 | Crystalline Form B of monophosphate |
| Crystalline Form B of monophosphate | FaSSIF | 4 | Crystalline Form B of monophosphate |
| Crystalline Form B of monophosphate | FeSSIF | 4 | Crystalline Form B of monophosphate |
| Crystalline Form B of monophosphate | H$_2$O | 24 | Crystalline Form B of monophosphate |
| Crystalline Form B of monophosphate | SGF | 24 | Crystalline Form B of monophosphate |
| Crystalline Form B of monophosphate | FaSSIF | 24 | Crystalline Form B of monophosphate |
| Crystalline Form B of monophosphate | FeSSIF | 24 | Crystalline Form B of monophosphate |

The results above show that crystalline Form A of monophosphate of the disclosure is stable in water, FaSSIF and FeSSIF after 1, 4, and 24 hours, and crystalline Form B of monophosphate do not change in all of the four kinds of media. However, the diphosphonate in CN102159570B convert into Form B of monophosphate after being equilibrated for 1 hour in the four media. The results indicate that the diphosphonate in CN102159570B is not stable in solvents containing water or biological medium, and the stability of the monophosphate of the disclosure which is more suitable for drug development is better than that of the diphosphonate in CN102159570B.

Example 10

Figure 10:
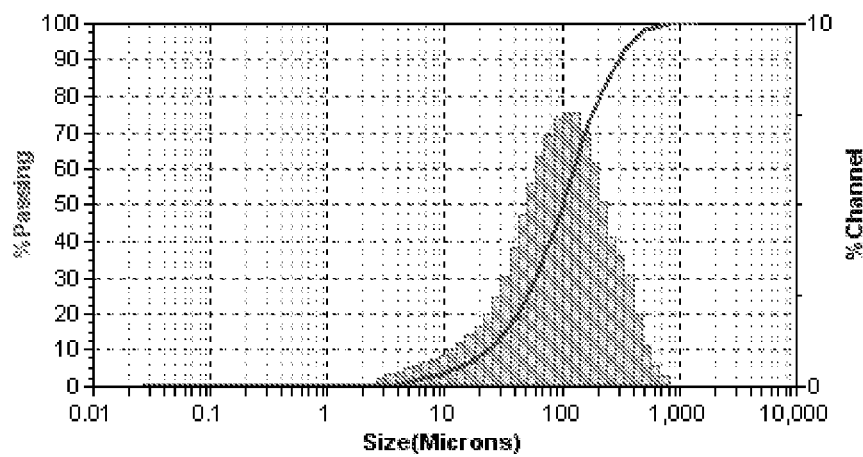
FIG. 10 shows the PSD diagram of crystalline Form A of monophosphate.
Figure 11:
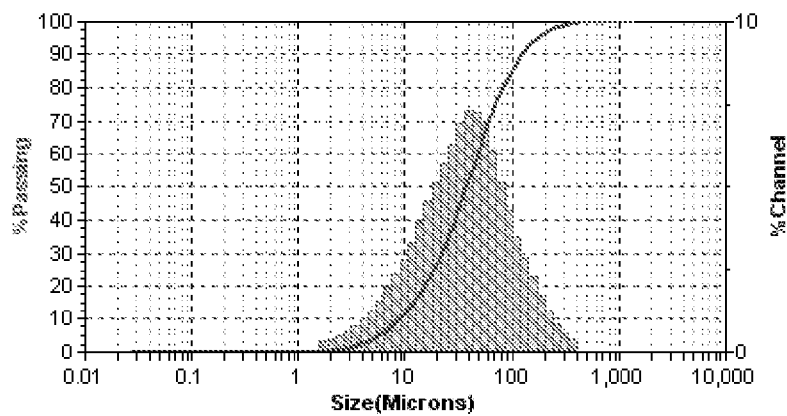
FIG. 11 shows the PSD diagram of crystalline Form B of monophosphate.

10-30 mg sample was dispersed with 10 mL Isopar G (containing 0.2% of lecithin). The sample is added into the SDC sample injection system when fully mixed. Start the experiment when the sample amount indication chart reaches a proper position. The result of particle size distribution test is shown in table 13, the particle size distribution diagram of the Form A is shown in FIG. 10, and the particle size distribution diagram of the Form B of monophosphate is shown in FIG. 11.

TABLE 13

Result of particle size distribution test

| Sample | MV (um) | SD (um) | D10 (um) | D50 (um) | D90 (um) |
|---|---|---|---|---|---|
| Crystalline Form A of monophosphate | 136.5 | 101.4 | 22.7 | 100.2 | 305.2 |
| Crystalline Form B of monophosphate | 55.4 | 40.7 | 8.8 | 37.5 | 124.2 |

Mv: Average particle size calculated by volume.
SD: Standard deviation
D10: Particle size which accounts for 10% of the particle size distribution (volume distribution).
D50: Particle size which accounts for 50% of the particle size distribution (volume distribution), also known as the median diameter.
D90: Particle size which accounts for 90% of the particle size distribution (volume distribution).

The test result shows that Form A and Form B have homogeneous particle size and good dispersion.

The invention claimed is:

1. A monophosphate of formula (I):

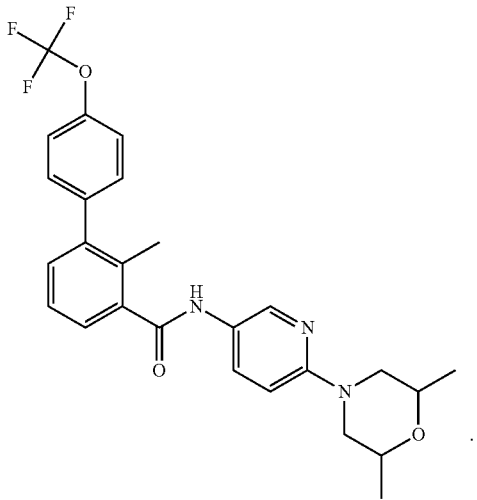

2. A crystalline Form A of the monophosphate of formula (I) according to claim 1, wherein the X-ray powder diffraction pattern shows characteristic peaks at 2theta values of 17.5°±0.2°, 5.1°±0.2° and 13.0°±0.2°.

3. The crystalline Form A of the monophosphate of formula (I) according to claim 2, wherein the X-ray powder diffraction pattern further shows one or two or three of the characteristic peaks at 2theta values of 18.0°±0.2°, 16.3°±0.2° and 24.4°±0.2°.

4. The crystalline Form A of the monophosphate of formula (I) according to claim 2, wherein the X-ray powder diffraction pattern further shows one or two or three of the characteristic peaks at 2theta values of 20.5°±0.2°, 9.8°±0.2° and 13.9°±0.2°.

5. A process of preparing crystalline Form A of the monophosphate of formula (I) according to claim 2, comprising reacting the compound of formula (I) with concentrated phosphoric acid in water or solvents containing water, and drying the obtained solid at 100° C.-200° C.

6. The process of preparation according to claim 5, wherein said solvents containing water comprise solvents of alcohols, ketones, esters, aromatic hydrocarbons, halogenated hydrocarbons, nitriles, cyclic ethers, aliphatic hydrocarbons mixed with water.

7. A process of preparing crystalline Form A of the monophosphate of formula (I) according to claim 2, comprising adding the hydrochloride of compound of formula (I) into one or more solvents selected from the group of water, alcohols, ketones, acids, esters or nitriles, and then adding sodium hydroxide solution, stirring to obtain a solid, reacting the obtained solid with concentrated phosphoric acid in water or solvents containing water, then drying the obtained solid at the temperature of 100-200° C.

8. The process of preparing crystalline Form A according to claim 7, wherein said alcohol is methanol.

9. The process of preparing crystalline Form A according to claim 7, wherein said solvents contain water and comprise solvents of alcohols, ketones, esters, aromatic hydrocarbons, halogenated hydrocarbons, nitriles, cyclic ethers, or aliphatic hydrocarbons mixed with water.

10. A crystalline Form B of monophosphate of formula (I) according to claim 1, wherein the X-ray powder diffraction pattern shows characteristic peaks at 2theta values of 19.2°±0.2°, 9.7°±0.2° and 16.5°±0.2°.

11. The crystalline Form B according to claim 10, wherein the X-ray powder diffraction pattern further shows one or two or three of the characteristic peaks at 2theta values of 19.6°±0.2°, 29.6°±0.2° and 12.6°±0.2°.

12. The crystalline Form B according to claim 10, wherein the X-ray powder diffraction pattern further shows one or two or three of the characteristic peaks at 2theta values of 17.2°±0.2°, 15.4°±0.2° and 25.0°±0.2°.

13. A process of preparing crystalline Form B according to claim 10, comprising reacting the compound of formula (I) with concentrated phosphoric acid in water or solvents containing water, and drying the obtained solid at 50° C.-80° C.

14. The process according to claim 13, wherein said solvents containing water comprise solvents of alcohols, ketones, esters, aromatic hydrocarbons, halogenated hydrocarbons, nitriles, cyclic ethers, aliphatic hydrocarbons mixed with water.

15. A process of preparing crystalline Form B according to claim 10, comprising adding the hydrochloride of compound of formula (I) into one or more solvents selected from the group of water, alcohols, ketones, acids, esters or nitriles, then stirring and crystallizing at the temperature of 50-80° C.

16. The process according to claim 15, wherein said acid is acetic acid, said nitrile is acetonitrile, said ketone is acetone, and said alcohol is methanol.

17. A process of preparing crystalline Form B according to claim 10, comprising adding the hydrochloride of compound of formula (I) into one or more solvents selected from the group of water, alcohols, ketones, acids, esters or nitriles, then adding sodium hydroxide solution, stirring to obtain a solid, reacting the obtained solid with concentrated phosphoric acid in water or solvents containing water, then drying the obtained solid at the temperature of 50-80° C.

18. The process according to claim 17, wherein said alcohol is methanol.

19. The process according to claim 17, wherein said solvents containing water comprise solvents of alcohols, ketones, esters, aromatic hydrocarbons, halogenated hydrocarbons, nitriles, cyclic ethers, aliphatic hydrocarbons mixed with water.

20. A pharmaceutical composition comprising an effective amount of the the monophosphate of formula (I) according to claim 1 and a pharmaceutically acceptable carrier, diluent or excipient.

21. A pharmaceutical composition comprising an effective amount of the crystalline Form A of the monophosphate of formula (I) according to claim 2, and a pharmaceutically acceptable carrier, diluent or excipient.

22. A pharmaceutical composition comprising an effective amount of the crystalline Form B of the monophosphate of formula (I) according to claim 10, and a pharmaceutically acceptable carrier, diluent or excipient.

* * * * *